Figure 1:
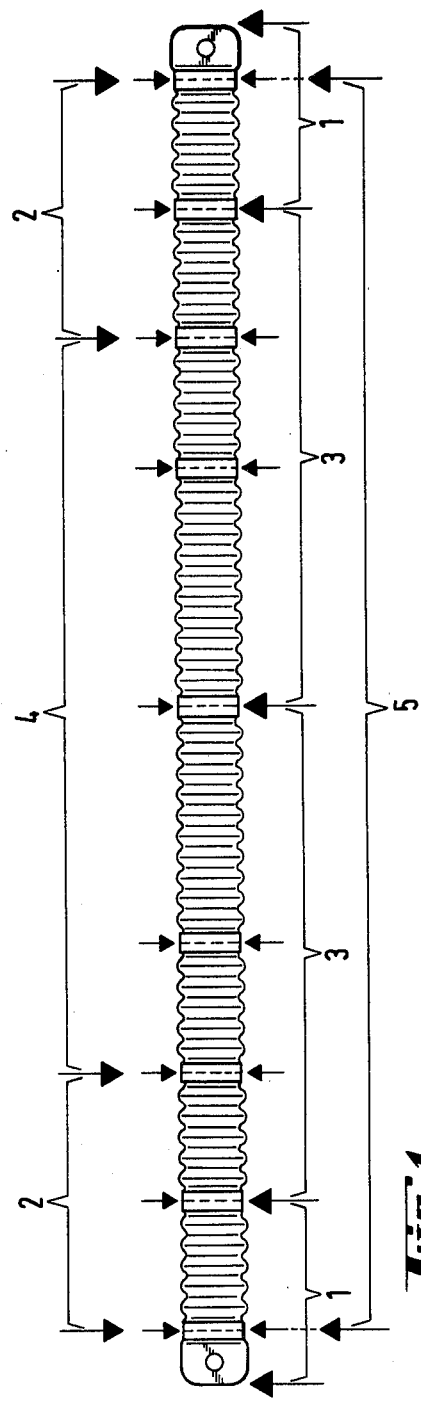

United States Patent [19]

Lang

[11] 4,360,104
[45] Nov. 23, 1982

[54] UNIVERSAL STERILE CLOSED HOSE SYSTEM FOR RESPIRATION THERAPY APPARATUS

[76] Inventor: Volker Lang, Spitzwegstrasse 63, 8012 Ottobrunn, Fed. Rep. of Germany

[21] Appl. No.: 180,030

[22] Filed: Aug. 21, 1980

[30] Foreign Application Priority Data

Aug. 29, 1979 [DE] Fed. Rep. of Germany ....... 2934916

[51] Int. Cl.³ ...................... B65D 85/08; B65D 85/62; B65D 69/00
[52] U.S. Cl. .................................. 206/527; 138/109; 138/121; 206/438; 206/820
[58] Field of Search ............ 206/526, 223, 438, 45.34, 206/527, 390, 0.7, 820, 806; 138/109, 121; 285/4

[56] References Cited
U.S. PATENT DOCUMENTS 2,974,825  3/1961  Ross ................................ 206/45.34
2,975,888  3/1961  Paynton, Sr. .................... 206/45.34
2,999,497  9/1961  Hamilton et al. ................... 138/121
3,234,969  2/1966  DuMont .............................. 138/121
3,838,713  10/1974 Tubbs .................................. 138/109

*Primary Examiner*—William T. Dixson, Jr.
*Attorney, Agent, or Firm*—Morgan, Finnegan, Pine, Foley & Lee

[57] ABSTRACT

A sterile hose set for use in apparatus for artificial respiration and for respiration-assisting and aerosol therapies consists of a tubular container, which is totally enclosed and internally sterile and has been made in one step from plastic material by blowing with sterile air. The hose set consists of a plurality of successive hose sections, which differ in length and are smooth-surfaced or pleated and are joined in a unit. Each of said hose sections is provided at both ends with special adapters. The terminal hose sections are closed at one end and provided at the other end with a special adapter. Disconnects are provided between the hose sections and at the ends of the hose set.

7 Claims, 4 Drawing Figures

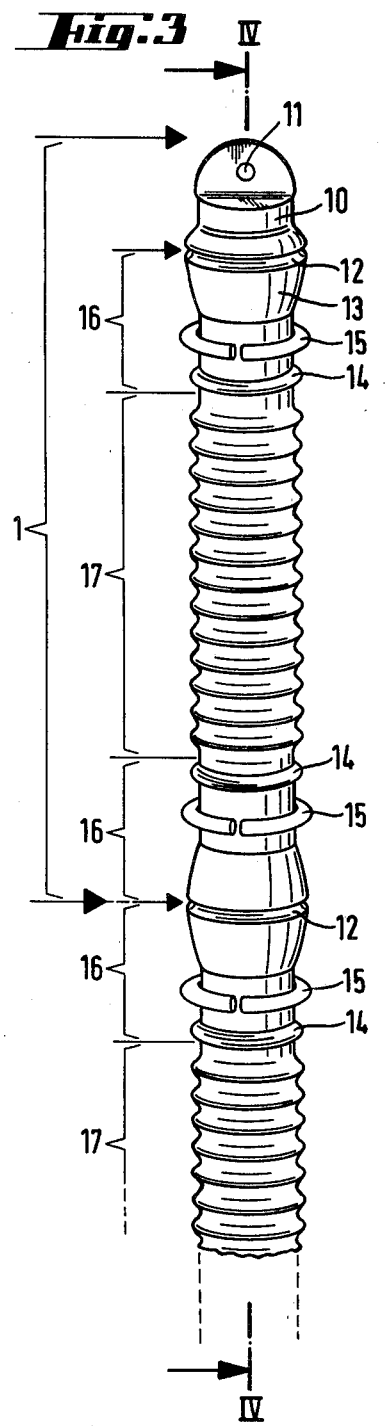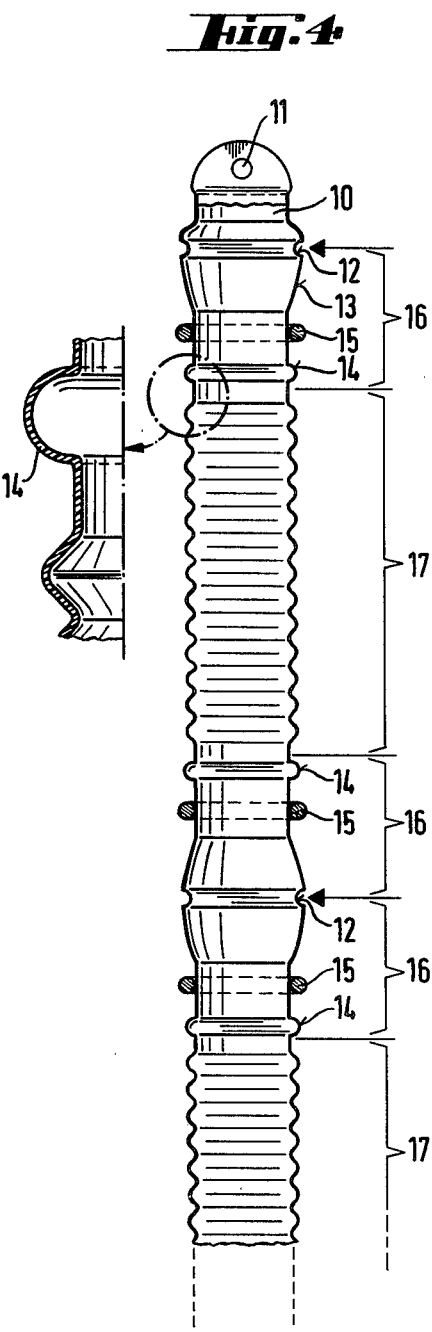

UNIVERSAL STERILE CLOSED HOSE SYSTEM FOR RESPIRATION THERAPY APPARATUS

This invention relates to sterile hose sets for use in apparatus for artificial respiration and for respiration-assisting and aerosol therapies.

In view of the increasing resistance of bacteria to antibiotics (infectious hospitalism), it has become absolutely necessary in the above-mentioned therapies in recent years to prevent by every means an infection of the patient. For this purpose it has been proposed to supply those parts which will directly contact the patient, particularly breathing hoses, in an inherently sterile condition for single use. That proposal has proved to be highly desirable from the medical and bacteriological aspects but involves high costs.

The manufacture of the breathing hoses presently offered for single use comprises the following steps;

1. Manufacture of the breathing hose of plastic material in different lengths and with different adapters, e.g., by extrusion or blowing;
2. Wrapping in plastic films (bonded by welding);
3. Sterilizing, particularly by gamma irradiation or by a treatment with ethylene oxide gas.

All steps required in addition to the manufacture of the plastic hoses add appreciably to the cost of the final product. For this reason, the therapeutic use of such hoses on a large scale is difficult or even impossible although it would be desirable from the aspects of hygiene and bacteriology.

It is an object of the present invention to provide sterile breathing hoses for single use which can be made at low cost. In accordance with the invention this object is accomplished in that the hose set consist of a tubular container, which is totally enclosed and internally sterile and has been made in one step from plastic material by blowing with sterile air and consists of a plurality of serially arranged hose sections, which differ in length and are smooth-surfaced or pleated and are joined in an unit, each of said hose sections is provided at both ends with special adapters, the terminal hose sections are closed at their outer ends, and disconnects are provided between the hose sections and near the ends of the hose set.

The plastic breathing hoses in different lengths which are required for an artificial respiration system to be assembled are connected in series at their special adapters and constitute an integral hose, which may have any desired length and is closed at both ends so that it constitutes a closed hollow body, which will be described hereinafter as a hose set.

These hose sets are made in a special blowing process. At the high temperatures in excess of 160° C. required to deform the plastic material in the manufacture of plastic parts, the material is sterilized. The additional use of sterile blowing air or another blowing gas permits the provision of sterile conditions inside the hose sets which have been made. As the hose sets constitute enclosed hollow bodies, they will remain internally sterile for a long time even without an additional packaging.

It is apparent that the sterile plastic breathing hoses can be made in any desired length as enclosed hose sets in a single step in a blowing process using sterile air or another sterile gas.

The user of the hoses must only divide the hose set at the marks which have been provided during the manufacture and will thus obtain the desired internally sterile tube sections to be used in the sterile artificial breathing system he desires to assemble. This separation of the tube sections may be facilitated by disconnect threads or strips or grooves which have been provided in the hose set by the manufacturer.

The terminal end closures of the hose set may be provided with hangers so that the user can more easily sever the required hose sections under sterile conditions.

In accordance with special requirements of the various elements to be connected in an artificial respiration system, such as the humidifier, artificial respiration head, Y-fitting, valves etc., the adapters of the hose sections may differ in diameter and length and may be provided with locking means, such as snap-in grooves or the like.

To facilitate the fitting of the adapters of the hose sections, said adapters may flare. As the adapters of the plastic hose sections just as the hose sections themselves consist mainly of physiologically and ecologically innocuous polyethylene or polypropylene, i.e., of plastic material which is not elastic and can easily be permanently deformed by mechanical action, e.g., as they are fitted on a tubular member and particularly when they are supplied with heat, e.g., from a heated humidifier for the gas to be inhaled, there is a risk that leaks develop at the hoses or that the hoses slip off. This problem can be solved in that the adapters are provided with snap-in grooves which prevent the adapters from slipping off. The required sealing action can be ensured by hose clips or spring rings which are applied and firmly and elastically force the hose section adapter onto another part of the artificial respiration system. Before the blowing operation these spring rings can be inserted into the mold and will then be properly and captively positioned in the hose set made by blow-molding.

The walls of the hose sections of the hose sets may have various shapes. For instance, they may be smooth or formed with ribs or pleats and may have different diameters.

Figure 2:
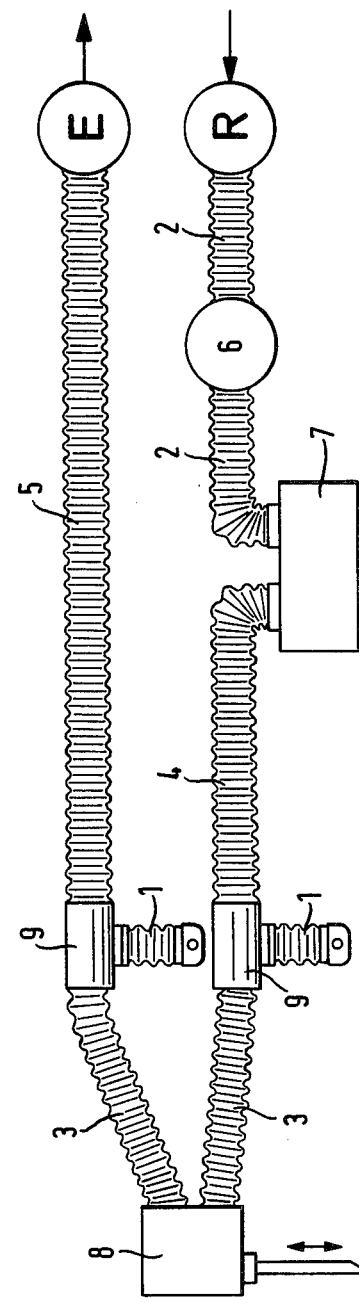

An embodiment of the invention will now be described by way of example with reference to the accompanying drawings, in which FIGS. 1 and 2 are diagrammatic views showing the possible variations and optimal utilization of the hose sets in an assembled artificial respiration system, FIG. 3 is a perspective view showing a hose section and an end portion of the hose set of FIG. 1 and FIG. 4 is a section taken long line I—I in FIG. 3.

FIG. 1 is a diagrammatic view showing a hose set. Disconnect grooves 12 at which hose sections can easily be separated are indicated by dotted lines and small arrows.

The end closure 10 in combination with a pleated hose section 17 and adapters 16 shown in FIG. 3 constitutes terminal hose section 1, which is succeeded by additional hose sections provided with adapters 16 at both ends. A disconnect groove 12 is provided between adjacent adapters. Each of the hoses 2, 3, 4 and 5 together with the adapters provided at the opposite ends of each hose section has an overall length of 25, 50, 75 or 125 cm, respectively. It is apparent from the diagrammatic showing in FIG. 1 that and how hoses differing in length can be most economically used in that a hose set is divided.

FIG. 2 shows diagrammatically a complete sterile artificial respiration system comprising hose sections of different lengths which have been obtained from three hose sets and serve to connect a bacteria filter 6, a heated humidier 7 for the air to be inhaled, T-fittings 9 provided with end section 1 as a condensate trap and the artificial respiration head 6 with a tracheal tube for connection to a patient. Gas to be inhaled is blown from a respirator or breathing machine R through 2, 6, 2, 7, 4, 9, 3 and 8 into the patient's lungs. The exhaled air flows through 3, 9, 5 to an exhalation valve E, which is controlled by the respirator.

FIG. 3 shows in perspective the peculiar details of a hose set consisting of terminal sections 1 and intermediate hose sections. The end closure 10 is formed by hose walls which have been flattened and joined by welding and is provided with a hanger consisting of an eyelet 11. Behind the end closure 10, the terminal section 1 comprises a tubular portion, which flares in bell shape. When the end closure 10 has been removed, this flaring portion of the terminal section 1 constitutes a flaring socket 13 at the disconnect groove 12 to facilitate the fitting of the hose section to another part of the artificial respiration system. The flaring socket 13 is succeeded by a straight, smooth tubular portion, which has a snap-in groove 14 and an open spring ring 15 for ensuring a tight seal and preventing the straight tubular portion from slipping off.

Elements 13 and 14 together constitute a hose adapter 16, which is succeeded by a pleated hose section 17, which at its opposite end merges into another adapter 16.

A disconnect groove is provided between two adjacent adapters. The different lengths of the hose sections have been diagrammatically indicated in FIG. 1.

The details which have been described are shown in section in FIG. 4.

What is claimed is:

1. A closed sterile hose set for apparatus for artificial respiration and for respiration-assisting and aerosol therapies, comprising serially arranged plural tubular hose sections, each said section having an adapter at each end, for inter-connection of artificial respiration, respiration-assisting and aerosol therapy apparatus components, said sterile hose set further comprising a disconnect between each pair of adjacent hose sections and at least two terminal hose sections, each said terminal hose section being closed at one end and provided with a disconnect near said closed end.

2. A sterile hose set as claimed in claim 1, wherein each hose section adapter has flaring end portions.

3. A hose set as claimed in claim 2 wherein each hose section adapter has a snap-in groove to prevent the adapter from slipping off.

4. A hose set as claimed in claim 3 wherein a spring ring of plastic material or metal is captively provided on each hose adapter between the flaring end portion and the snap-in groove.

5. A hose set as claimed in claim 3 wherein each hose adapter tapers to a smaller diameter behind the snap-in groove to serve as a reducer.

6. A hose set as claimed in claim 1 wherein the end portions of the terminal hose sections are flattened in a length of about 2 to 3 cm and the flattened plies are joined by welding and are provided with a hanger.

7. A hose set as claimed in claim 1 wherein the disconnects consist of simple grooves or are additionally provided with a separating thread or strip.

* * * * *